US00PP37768P2

(12) United States Plant Patent
van Dijk

(10) Patent No.: US PP37,768 P2
(45) Date of Patent: Oct. 13, 2026

(54) ***ANTHURIUM* PLANT NAMED 'AN2414664'**

(50) Latin Name: *Anthurium andreanum*
Varietal Denomination: AN2414664

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/559,931

(22) Filed: Mar. 6, 2026

(51) Int. Cl.
*A01H 5/02* (2018.01)
*A01H 6/10* (2018.01)

(52) U.S. Cl.
USPC ..... Plt./368

(58) Field of Classification Search
USPC ..... Plt./263.1, 365, 368
See application file for complete search history.

(56) References Cited

U.S. PATENT DOCUMENTS

PP36,272 P2 * 11/2024 van Dijk ..... Plt./365

* cited by examiner

*Primary Examiner* — Karen M Redden
(74) *Attorney, Agent, or Firm* — C. Anne Whealy

(57) ABSTRACT

A new and distinct cultivar of Anthurium plant named 'AN2414664', characterized by its compact, upright to outwardly arching plant habit; freely clumping growth habit; bushy and dense plants; narrowly cordate dark green-colored leaves; freely flowering habit; inflorescences that are positioned above the foliar plane on sturdy scapes; broadly cordate spathes that are dark reddish brown in color; and spadices that are purple in color with brown-colored apices.

2 Drawing Sheets

Figure 1:
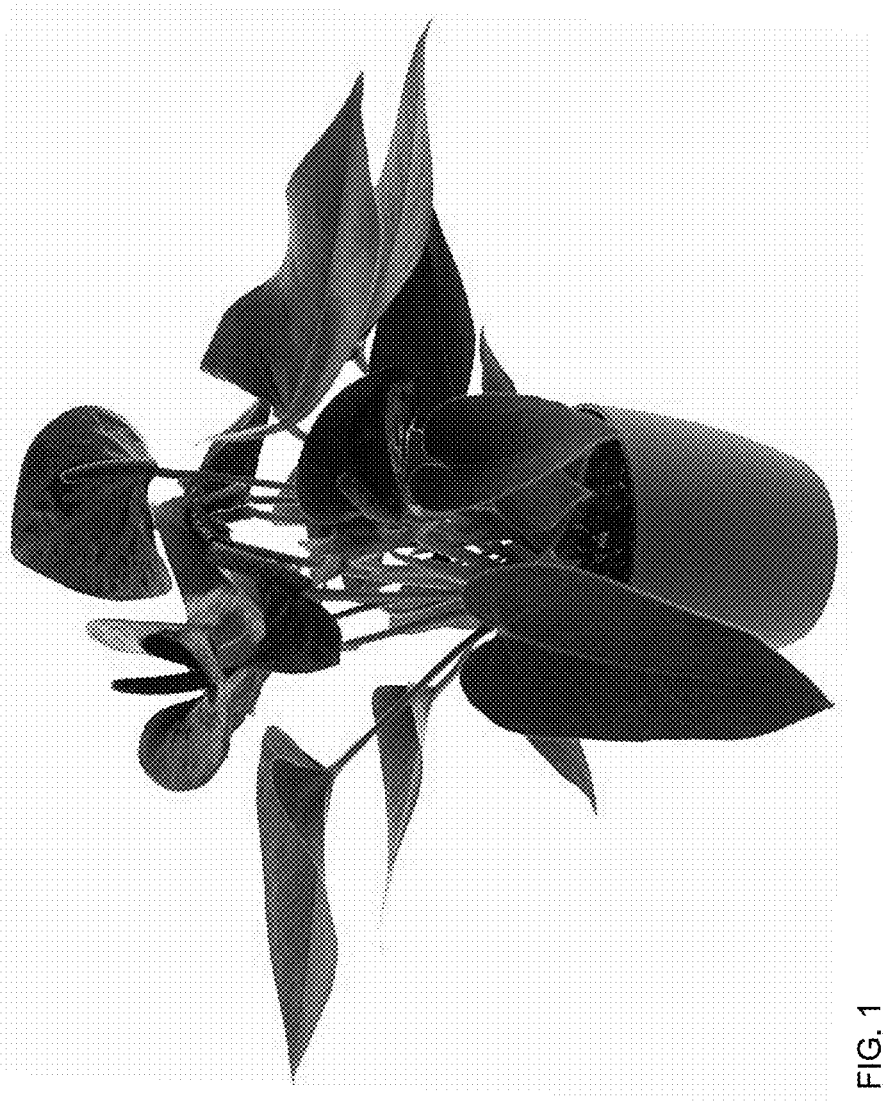

Botanical designation: *Anthurium andreanum.*
Cultivar denomination: 'AN2414664'.

A European Community Plant Breeder's Rights application for the instant plant was filed by the Applicant/Assignee of the instant application, Anthura B.V. of Bleiswijk, The Netherlands on Nov. 20, 2024, application No. 2024/2700. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2414664'.

The new *Anthurium* plant is a product of a controlled breeding program conducted by the Inventor in Bleiswijk, The Netherlands. The objective of the breeding program is to create new compact *Anthurium* plants with durable dark reddish brown-colored spathes.

The new *Anthurium* plant originated from a cross-pollination made by the Inventor in January 2014 in Bleiswijk, The Netherlands of a proprietary breeding selection of Anthurium andreanum identified as code No. 09-022992-0010, not patented, as the female, or seed, parent with a proprietary breeding selection of *Anthurium andreanum* identified as code No. 09-023435-0001, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in December 2015.

Asexual reproduction of the new *Anthurium* plant by in vitro meristem propagation in a controlled environment in Bleiswijk, The Netherlands since June 2017 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2414664'. These characteristics in combination distinguish 'AN2414664' as a new and distinct *Anthurium* plant:

1. Compact, upright to outwardly arching plant habit.
2. Freely clumping growth habit; bushy and dense plants.
3. Narrowly cordate dark green-colored leaves.
4. Freely flowering habit.
5. Inflorescences that are positioned above the foliar plane on sturdy scapes.
6. Broadly cordate spathes that are dark reddish brown in color.
7. Spadices that are purple in color with brown-colored apices.

Plants of the new *Anthurium* differ primarily from plants of the female parent selection in the following characteristics:

1. Plants of the new *Anthurium* are more compact than plants of the female parent selection.
2. Spadices of plants of the new *Anthurium* are purple in color with brown-colored apices whereas spadices of plants of the female parent selection are white in color with yellowish green-colored apices.

Plants of the new *Anthurium* differ primarily from plants of the male parent selection in the following characteristics:

1. Spathes of plants of the new *Anthurium* are glossier than spathes of plants of the male parent selection.
2. Spadices of plants of the new *Anthurium* are purple in color with brown-colored apices whereas spadices of plants of the male parent selection are red purple in color.

Plants of the new *Anthurium* can also be compared to plants of *Anthurium andreanum* 'AN2142228', disclosed in U.S. Plant Pat. No. 36,272. In side-by-side comparisons, plants of the new *Anthurium* differ primarily from plants of 'AN2142228' in the following characteristics:

1. Leaves of plants of the new *Anthurium* have smaller proximal lobes than leaves of plants of 'AN2142228'.
2. Spadices of plants of the new *Anthurium* are shorter spadices of than plants of 'AN2142228'.

BRIEF DESCRIPTION OF THE PHOTOGRAPHS

The accompanying photographs illustrate the overall appearance of the new *Anthurium*.

The photographs show the colors as true as it is reasonably possible to obtain in colored reproductions of this type.

Colors in the photographs may differ slightly from the color values cited in the detailed botanical description which accurately describe the colors of the new *Anthurium*.

The photograph on the first sheet (FIG. 1) is a side perspective view of a typical plant of 'AN2414664' grown in a container.

Figure 2:
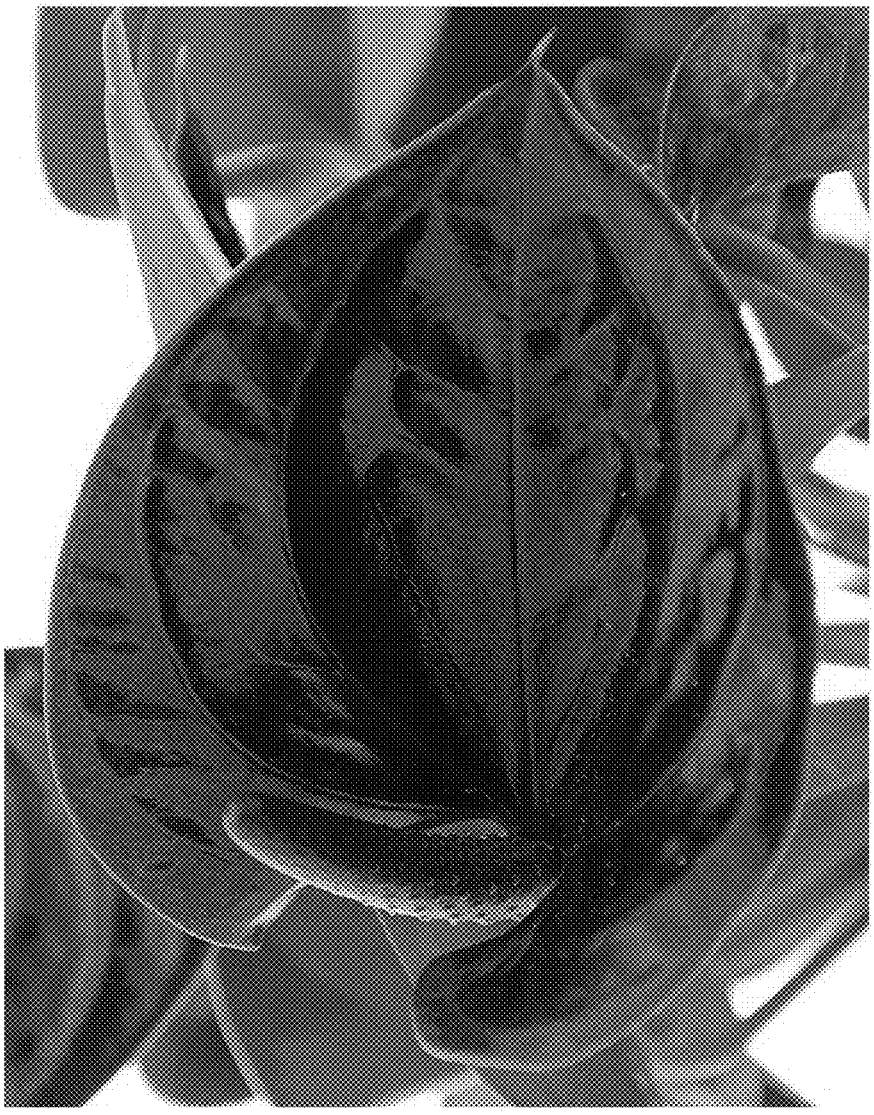

The photograph on the second sheet (FIG. 2) is a close-up view of a typical inflorescence of 'AN2414664'.

DETAILED BOTANICAL DESCRIPTION

The aforementioned photographs and following observations and measurements describe plants grown in 9-cm containers during the early autumn in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 umol to about 200 umol. Plants were nine months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2414664'.

Parentage:

*Female, or seed, parent.*—Proprietary breeding selection of *Anthurium andreanum* identified as code No. 09-022992-0010, not patented.

*Male, or pollen, parent.*—Proprietary breeding selection of *Anthurium andreanum* identified as code No. 09-023435-0001, not patented.

Propagation:

*Type.*—By in vitro meristem propagation.

*Time to initiate roots, summer and winter.*—About two weeks at temperatures ranging from about 19° C. to about 22.5° C.

*Time to produce a rooted young plant, summer and winter.*—About six to eight weeks at temperatures ranging from about 19° C. to about 22.5° C.

*Root description.*—Medium in thickness, fibrous; typically creamy white in color; actual color of the roots is dependent on substrate composition, water quality, fertilizer type and formulation, substrate temperature and physiological age of roots.

*Rooting habit.*—Freely branching, medium density.

Plant description:

*Plant shape.*—Compact, upright to outwardly arching plant habit;

overall shape, flattened globular.

*Growth habit.*—Freely clumping habit imparting a bushy and dense appearance; in a single year of production, about 40 individual plants can be harvested per plant; moderately vigorous growth habit and moderate growth rate.

*Plant height, from soil level to top of leaf plane.*—About 16.9 cm.

*Plant height, from soil level to top of inflorescences.*—About 19.7 cm.

*Plant diameter or spread.*—About 31.7 cm.

Leaf description:

*Arrangement.*—Alternate; simple.

*Length.*—About 13.7 cm.

*Width.*—About 7.3 cm.

*Shape.*—Narrowly cordate.

*Apex.*—Narrowly apiculate with a small mucronate tip.

*Base.*—Cordate.

*Margin.*—Entire; slightly and coarsely undulate.

*Texture, upper and lower surfaces.*—Smooth, glabrous; moderately coriaceous.

*Venation pattern.*—Pinnate.

*Color.*—Developing leaves, upper surface: Close to 146A strongly tinged with close to 152B; narrow marginal edges, close to 199A; mucronate tip, close to 151A. Developing leaves, lower surface: Close to 146A; narrow marginal edges, close to N199C; mucronate tip, close to 151A. Fully expanded leaves, upper surface: Close to a blend of 139A and N189A; narrow marginal edges, close to 143A; mucronate tip, close to 143A; venation, close to NN137B. Fully expanded leaves, lower surface: Close to a blend of 143A and 146A; venation, close to N144A.

*Petioles.*—Length: About 8.7 cm. Diameter: Distally, about 2.5 mm and proximally, about 4mm. Texture, upper and lower surfaces: Smooth, glabrous. Color, upper surface: Close to a blend of 137C and 143A. Color, lower surface: Close to a blend of 144A and 146A. Geniculum length: About 1.5 cm. Geniculum diameter: About 3.5 mm. Geniculum texture, upper and lower surfaces: Smooth, glabrous. Geniculum color, upper surface: Close to NN137C; ridges, close to N199A. Geniculum color, lower surface: Close to 144A. Wing length: About 1.3 cm. Wing diameter: About 4 mm. Wing texture: Smooth, glabrous. Wing color, upper and lower surfaces: Close to 143A; towards the margins, close to 144C.

Inflorescence description:

*Inflorescence arrangement and flowering habit.*—Spathes with spadices; open inflorescences held above the foliar plane on sturdy scapes; flowering structures arise from leaf axils; freely and continuous flowering year-round in controlled temperature greenhouses in The Netherlands; typically about eight developing and developed inflorescences per plant at one time; inflorescence development commences about 2.5 to 3.5 months after planting rooted young plants.

*Inflorescence longevity.*—On the plant, depending on temperature, spathes maintain good substance for about two months; inflorescences persistent.

*Fragrance.*—None detected.

*Spathes.*—Length: About 7.8 cm. Width: About 7.8 cm. Shape: Broadly cordate to close to reniform; slightly to strongly carinate. Apex: Acute with a short mucronate apex. Base: Cordate. Margin: Entire; coarsely undulate. Aspect: About 50° to 95° from the scape axis. Texture, upper and lower surfaces: Smooth, glabrous; moderately coriaceous. Color: When developing, front surface: Close to a blend of 187A and 187B; at the base, tinged with close to 146B and 146C; venation, close to 185A. When developing, rear surface: Close to 183A; at the base, tinged with close to 146B; main vein, close to 179A. Fully developed, front surface: Close to a blend of 187A and 200A; at the base, slightly tinged with close to 146A; with subsequent development, color becoming closer to 200A and at the base, tinged with close to 143A. Fully developed, rear surface: Close to 175A; towards the base, close to 146A; narrow marginal edges, close to 185A; main vein, close to N34A; with subsequent development, color becoming closer to a blend of 175A and 175B and towards the base, close to a blend of 143A and 143B with narrow marginal edges, close to N186C.

*Spadices.*—Length: About 3.6 cm. Diameter: About 7 mm. Shape: Cylindrical, slightly tapering towards the apex; apex, obtuse; base, obtuse; in cross-section, rounded. Aspect: Erect to about 20° from the scape axis. Color, immature: Close to a blend of 175A and 200D; towards the apex, close to 175A. Color, mature: Close to N187B; towards the apex, close to N199A. Flowers: Type: Hermaphroditic. Quantity per spadix: About 140.Height: About 1 mm. Diameter: About 2.5 mm. Shape: Roughly square. Anther color: Close to N187B. Pollen amount: Moderate. Pollen color: Close to NN155A. Stigma color: Close to N200C. Ovary color: Close to 184A.

*Scapes.*—Length: About 11.5 cm. Diameter: About 3 mm. Strength: Sturdy. Aspect: About 15° from vertical. Color: Close to 144A; distally, close to 175A and 175B.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2414664' as herein illustrated and described.

* * * * *